(12) United States Patent
Lim et al.

(10) Patent No.: US 11,077,219 B2
(45) Date of Patent: Aug. 3, 2021

(54) STERILIZATION APPARATUS UTILIZING SEALING POUCH AND VACUUM CONTAINER

(71) Applicant: Plasmapp Co., Ltd., Daejeon (KR)

(72) Inventors: Youbong Lim, Daejeon (KR); Jaejun Hawn, Daejeon (KR)

(73) Assignee: PLASMAPP CO., LTD., Daejeon (KR)

( * ) Notice: Subject to any disclaimer, the term of this patent is extended or adjusted under 35 U.S.C. 154(b) by 0 days.

(21) Appl. No.: 16/125,259

(22) Filed: Sep. 7, 2018

(65) Prior Publication Data

US 2019/0001008 A1    Jan. 3, 2019

Related U.S. Application Data

(63) Continuation of application No. PCT/KR2016/015256, filed on Dec. 26, 2016.

(30) Foreign Application Priority Data

Jul. 11, 2016  (KR) .......................... 10-2016-0087286

(51) Int. Cl.
*A61L 2/14*    (2006.01)
*A61L 2/20*    (2006.01)
(Continued)

(52) U.S. Cl.
CPC ................. *A61L 2/208* (2013.01); *A61L 2/04* (2013.01); *A61L 2/14* (2013.01); *A61L 2/20* (2013.01);
(Continued)

(58) Field of Classification Search
CPC ..... A61L 2/04; A61L 2/14; A61L 2/20; A61L 2/208; A61L 2/24; A61L 2/26;
(Continued)

(56) References Cited

U.S. PATENT DOCUMENTS 5,160,700 A * 11/1992 Anderson ............... A61L 2/206
239/55
6,488,902 B1 * 12/2002 DeCato ..................... A61L 2/14
422/30
(Continued)

FOREIGN PATENT DOCUMENTS

EP    1 557 181 B1    6/2009
JP    11-221443 A     8/1999
(Continued)

OTHER PUBLICATIONS

Office Action issued in the German Patent Office in corresponding German Application No. 11 2016 006 510.8 dated Jan. 14, 2020.
(Continued)

*Primary Examiner* — Timothy C Cleveland
(74) *Attorney, Agent, or Firm* — Sughrue Mion, PLLC

(57) ABSTRACT

A sterilization method may include loading a vacuum wrapper containing and sealing a target object in a vacuum container, evacuating the vacuum container and the vacuum wrapper, injecting a sterilant into the vacuum wrapper, which is disposed in the vacuum container and is maintained at a vacuum state, and venting the vacuum container to allow it to have an atmospheric pressure.

13 Claims, 9 Drawing Sheets

(51) Int. Cl.
*A61L 2/26* (2006.01)
*B65D 65/40* (2006.01)
*A61L 2/04* (2006.01)

(52) U.S. Cl.
CPC ............. *A61L 2/26* (2013.01); *B65D 65/40* (2013.01); *A61L 2202/11* (2013.01); *A61L 2202/122* (2013.01); *A61L 2202/15* (2013.01); *A61L 2202/181* (2013.01); *A61L 2202/24* (2013.01)

(58) Field of Classification Search
CPC ............. A61L 2202/11; A61L 2202/12; A61L 2202/121; A61L 2202/122; A61L 2202/123; A61L 2202/15; A61L 2202/181; A61L 2202/182; A61L 2202/24; B65D 65/40
See application file for complete search history.

(56) References Cited

U.S. PATENT DOCUMENTS

2003/0108460 A1* 6/2003 Andreev ................ B01D 53/32
422/186.07
2005/0147527 A1* 7/2005 Brown .................... A61L 2/202
422/33
2006/0008378 A1* 1/2006 Imai ........................ A61L 2/208
422/28

FOREIGN PATENT DOCUMENTS

| | | |
|---|---|---|
| JP | 2005-279042 A | 10/2005 |
| JP | 2005-312799 A | 11/2005 |
| JP | 2011-235153 A | 11/2011 |
| WO | 2009/005252 A2 | 1/2009 |
| WO | 2016/028037 A1 | 2/2016 |

OTHER PUBLICATIONS

First Office Action issued in the Chinese Patent Office in corresponding Chinese Application No. 201680083341.7 dated Apr. 23, 2020.

Office Action dated Oct. 20, 2020 in Japanese Application No. 2018-559251.

Office Action dated Sep. 2, 2020 from the German Patent and Trademark Office in German Application No. 11 2016 006 510.8.

* cited by examiner

STERILIZATION APPARATUS UTILIZING SEALING POUCH AND VACUUM CONTAINER

CROSS-REFERENCE TO RELATED APPLICATIONS

The present application is a continuation of International Patent Application No. PCT/KR2016/015256, filed Dec. 26, 2016, which is based upon and claims the benefit of priority to Korean Patent Application No. 10-2016-0087286, filed on Jul. 11, 2016. The disclosures of the above-listed applications are hereby incorporated by reference herein in their entirety.

TECHNICAL FIELD

The present disclosure relates to a sterilization apparatus, and in particular, to a sterilization apparatus configured to sterilize a target object in a vacuum wrapper.

BACKGROUND ART

A chemical sterilizer is used to perform a sterilization process (for example, using hydrogen peroxide (H2O2) or chlorine dioxide (ClO2) gas as a sterilant) at a relatively low temperature.

In a conventional chemical sterilizer using hydrogen peroxide as the sterilant, the sterilant is supplied into a sterilization chamber, which is prepared to have a base vacuum pressure of less than 10 Torr. In such a vacuum state, the sterilant supplied is vaporized at a low temperature of 60° C. or lower. A supply amount of the sterilant is controlled in such a way that the pressure is preserved to a level of about 30 Torr by an amount of the sterilant to be diffused into the sterilization chamber. By controlling the vacuum level in this manner, it is possible to maintain hydrogen peroxide to a gaseous state under pressure and temperature conditions for a main step and to allow gaseous sterilant to pass through a wrapping film in the sterilization chamber and reach a target object or an article, during a sterilization process.

A convection-based heating process with low heat transfer efficiency is used to raise the temperature of the target object or article, which is disposed in the conventional chemical sterilizer, to a process temperature. For example, the heating process includes raising the temperature of the sterilization chamber to a process temperature (e.g., 60 degrees Celsius), and repeating a vacuum pumping process and a heated-air injection process. Here, the process temperature, one of the most important process parameters, should be controlled to ensure process reliability in the sterilization process. Thus, a process time for the heating process should be sufficiently increased so as to allow the sterilization chamber and the target article to reach a state of thermal equilibrium.

To prevent secondary and cross infection after the sterilization process, the sterilization process using the conventional sterilizer is perform on a target article wrapped within a pouch. For an effective sterilization process, one of surfaces of the pouch is generally formed of a selectively permeable material (e.g., TIVEK), while another surface is formed of a transparent film (e.g., PE, PET or PE-PET film) so that the target article in the pouch can be seen. Here, the selectively permeable material is selected to allow the sterilant to pass therethrough during the sterilization process and to be impermeable to microbe. Accordingly, the sterile state of the pouch can be maintained after the sterilization process. However, the sterilant may be partially absorbed in the TIVEK film during the sterilization process, and this may lead to some technical issues such as loss of sterilant and low efficiency in the sterilization process. Furthermore, the sterilant may be absorbed in a wrapping pouch film or remain on its surface, after the sterilization process. Thus, a purification process should be performed sufficiently to prevent a user from being exposed to such a residual sterilant.

After the sterilization process, the purification process for the user's safety is additionally performed on the sterilization chamber to remove the residual sterilant from an inner surface of the sterilization chamber, an inner space of the wrapping pouch film made of the conventional TIVEK, and the surface of the wrapping pouch film. For example, one of vacuumization, aeration, and plasma discharge processes may be performed as the purification process. However, such an indirect purification process has low efficiency in removing a residual sterilant from the target article, and thus, to ensure the user's safety, the purification process should be performed for a long time.

That is, there is an increasing demand for a fast and safe sterilization technology. According to some embodiments of the inventive concept, a sterilant is directly injected into a sealing-type pouch with an impermeable film. A vacuum chamber enclosing the sealing-type pouch is configured to expand an internal volume of the pouch using a pressure difference. Accordingly, it is possible to realize a fast and efficient sterilization process. Furthermore, since the sterilant is directly injected into the sealing-type pouch, it is possible to prevent the sterilant from remaining on an outer surface of the pouch to be in contact with a user. This makes it possible to omit the additional purification process and ensure the user's safety.

SUMMARY

Some embodiments of the inventive concept provide a sterilization process capable of overcoming technical issues (e.g., the limitation of sterilant permeability and the consequent slow sterilization issue), which occur in a conventional sterile packaging using a selectively permeable film (e.g., TIVEK).

Some embodiments of the inventive concept provide a technology for overcoming the issue of user safety, which may occur when a sterilant is absorbed in and remains on a selectively permeable film (e.g., TIVEK).

Some embodiments of the inventive concept provide a sterilization process, in which an impermeable film, not a selectively permeable film, is used. The use of the sterilization process may make it possible to realize a vacuum sealing and thereby maintain a sterile state for a long time after the sterilization process. In the sterilization process, a sterilant is directly injected into a wrapping pouch and a vacuum container disposed outside the pouch is used. These may make it possible to secure a volume of the pouch and effectively perform the sterilization process.

Some embodiments of the inventive concept provide a pouch, in which a nozzle is formed. The use of the pouch may make it possible to directly inject a sterilant into the pouch and to realize a vacuum sealing.

Some embodiments of the inventive concept provide a pouch configured to cause a plasma discharge on an inner surface of a pouch. The plasma discharge may be utilized to remove a sterilant remaining in the pouch, after a sterilization process.

According to some embodiments of the inventive concept, a sterilization method may include loading a vacuum wrapper containing and sealing a target object in a vacuum container, evacuating the vacuum container and the vacuum wrapper, injecting a sterilant into the vacuum wrapper, which is disposed in the vacuum container and is maintained at a vacuum state, and venting the vacuum container to allow it to have an atmospheric pressure.

In some embodiments, the method may further include evacuating the sterilant from the vacuum wrapper disposed in the vacuum container.

In some embodiments, the vacuum wrapper may be formed of a material preventing an external gas from permeating therein.

In some embodiments, the vacuum wrapper, in which the target object is disposed, may be sealed by a thermocompression method.

In some embodiments, the vacuum wrapper may include a connection member which is used to inject the sterilant into the vacuum wrapper and evacuate gas from the vacuum wrapper.

In some embodiments, a pressure of the vacuum wrapper may be higher than a base pressure of the vacuum container, when the sterilant is injected into the vacuum wrapper.

In some embodiments, a pressure of the vacuum wrapper may be substantially equal to a base pressure of the vacuum container, when the sterilant is evacuated from the vacuum wrapper.

In some embodiments, the vacuum wrapper may be heated to 50° C.-65° C. by a heater disposed in the vacuum container.

In some embodiments, the vacuum container and the vacuum wrapper may be evacuated at the same time.

In some embodiments, the injecting of the sterilant into the vacuum wrapper and the evacuating of the sterilant from the vacuum wrapper may be performed using a connection member disposed in the vacuum wrapper.

In some embodiments, the sterilant may be hydrogen peroxide whose concentration is 50 weight percent or higher.

According to some embodiments of the inventive concept, a sterilization method may include loading a vacuum wrapper containing and sealing a target object, in a vacuum container, evacuating the vacuum container and the vacuum wrapper, producing plasma in the vacuum wrapper, which is disposed in the vacuum container and is maintained at a vacuum state, and venting the vacuum container to allow it to have an atmospheric pressure.

In some embodiments, the method may further include injecting a sterilant into the vacuum wrapper, which is disposed in the vacuum container and is maintained at a vacuum state.

In some embodiments, the plasma may be produced by a dielectric barrier discharge.

In some embodiments, the method may further include evacuating the sterilant from the vacuum wrapper disposed in the vacuum container.

In some embodiments, the vacuum wrapper may be formed of a material preventing an external gas from permeating therein.

In some embodiments, the vacuum wrapper, in which the target object is disposed, may be sealed by a thermocompression method.

In some embodiments, the vacuum wrapper may include a connection member which is used to inject the sterilant into the vacuum wrapper and evacuate gas from the vacuum wrapper.

In some embodiments, a pressure of the vacuum wrapper may be higher than a base pressure of the vacuum container, when the sterilant is injected into the vacuum wrapper.

In some embodiments, a pressure of the vacuum wrapper may be substantially equal to a base pressure of the vacuum container, when the sterilant is evacuated from the vacuum wrapper.

In some embodiments, the vacuum wrapper may be heated to 50° C.-65° C. by a heater disposed in the vacuum container.

In some embodiments, the vacuum container and the vacuum wrapper may be evacuated at the same time.

In some embodiments, the injecting of the sterilant into the vacuum wrapper and the evacuating of the sterilant from the vacuum wrapper may be performed using a connection member disposed in the vacuum wrapper.

In some embodiments, the sterilant may be hydrogen peroxide whose concentration is 50 weight percent or higher.

According to some embodiments of the inventive concept, a sterilization apparatus may include a vacuum container, a vacuum wrapper loaded in the vacuum container to contain and seal a target object, a vacuum pump evacuating the vacuum container and the vacuum wrapper, a sterilant providing part injecting a sterilant into the vacuum wrapper, and an air injection part injecting air into the vacuum container. After the sterilant is injected into the vacuum wrapper, the vacuum container may be maintained at a vacuum state of a base pressure and a pressure of the vacuum wrapper may be higher than the base pressure.

In some embodiments, the vacuum wrapper may include a ground layer, a dielectric layer, and a conductive layer with a hole array pattern, which are sequentially stacked. The ground layer may be used as an outer film of the vacuum wrapper, and the conductive layer may be used as an inner film of the vacuum wrapper.

In some embodiments, the sterilization apparatus may further include an alternating current (AC) power which is provided outside the vacuum container and is used to supply an AC power to the ground layer and the conductive layer.

In some embodiments, the sterilant providing part may include a vaporizer, which is configured to heat and vaporize a sterilant that is supplied from an outside, a first valve between an output terminal of the vaporizer and a connection member of the vacuum wrapper, and a second valve between an output terminal of the vaporizer and an input terminal of the vacuum pump.

In some embodiments, the air injection part may include an air filter which is used to filter an outer air, a third valve between an input/output terminal of the vacuum container and an input terminal of the vacuum pump, and a fourth valve between the air filter and the input/output terminal of the vacuum container.

In some embodiments, the vacuum container may include at least one of a door, which is used to load the vacuum wrapper, a lower heater, which is disposed in the vacuum container and is used to load and heat the vacuum wrapper, and an upper heater, which is used to heat the vacuum container.

In some embodiments, the vacuum wrapper may include a connection member, which is used to supply the sterilant from an outside to the vacuum wrapper and to evacuate gas from an inner space of the vacuum wrapper. The connection member may be thermocompressed to the vacuum wrapper and may have a penetration hole, and a portion of the vacuum wrapper adjacent to the connection member may be thermocompressed after an evacuating process of the sterilant.

In some embodiments, the vacuum wrapper may include a lower film and an upper film, which are used to provide an internal space through a thermocompression process. The conductive layer may include a discharge region with a hole array pattern and a pad region extending from the discharge region. The upper film may include an opening which is formed to face the pad region, the adhesive film may be disposed to be aligned to the opening, a portion of the adhesive film may be in contact with the upper film adjacent to the opening and provides a sealed space, and another portion of the adhesive film may be in contact with the pad region and provides a sealed space.

In some embodiments, the sterilization apparatus may further include a power electrode connecting portion provided in the vacuum container and through the adhesive film, the power electrode connecting portion being in electric contact with the pad region, and a compression part provided around the power electrode connecting portion and used to press the adhesive film.

According to some embodiments of the inventive concept, a vacuum wrapper with a connection member may be provided. The connection member may be provided in the vacuum wrapper by a thermocompression method. The connection member may be used as a pathway for supplying and evacuating a sterilant to and from the vacuum wrapper through a coupling member, which is coupled to the connection member in the vacuum container. The connection member may be coupled to the coupling member, in the vacuum container, and a portion of the vacuum wrapper adjacent to the connection member may include a thermocompressed portion that is thermocompressed in the vacuum container, after an evacuating process of the sterilant.

According to some embodiments of the inventive concept, a vacuum wrapper with an upper film and a lower film may be provided. The lower film may include a ground layer, a dielectric layer, and a conductive layer with a hole array pattern, which are sequentially stacked. The ground layer may be used as an outer film of the vacuum wrapper, and the conductive layer may be used as an inner film of the vacuum wrapper. The vacuum wrapper may include a connection member provided by a thermocompression method, and the connection member may be used as a pathway for supplying and evacuating a sterilant to and from the vacuum wrapper through a coupling member, which is coupled to the connection member in the vacuum container. The connection member may be coupled to the coupling member, in the vacuum container, and a portion of the vacuum wrapper adjacent to the connection member may include a thermocompressed portion that is thermocompressed in the vacuum container, after an evacuating process of the sterilant.

In some embodiments, the conductive layer may include a discharge region with a hole array pattern and a pad region extending from the discharge region. The upper film may be provided to have an opening that is formed to face the pad region, and an adhesive film may be disposed to be aligned to the opening. A portion of the adhesive film may be in contact the upper film adjacent to the opening and provides a sealed space and another portion of the adhesive film may be in contact with the pad region and provides a sealed space.

According to some embodiments of the inventive concept, an impermeable film is used to directly inject a sterilant into a sealable wrapping pouch and thereby to improve efficiency of a sterilization process. Furthermore, the use of the impermeable film may make it possible to overcome an issue of user safety, which may occur when the sterilant is absorbed in a pouch film or remains on a surface of the pouch.

According to some embodiments of the inventive concept, an impermeable film is used to vacuumize and seal a wrapping pouch, after a sterilization process. This may make it possible to maintain a sterile state of the wrapping pouch for a longer time, compared with a wrapping pouch using a conventional semipermeability film.

According to some embodiments of the inventive concept, it is possible to produce plasma in a pouch. The plasma may be used to effectively heat a target article and purify a sterilant remaining in the pouch after a sterilization process. Accordingly, it is possible to realize an efficient and safe sterilization process.

According to some embodiments of the inventive concept, a plasma discharge in a vacuum container and a pouch is used to maximize process efficiency of a sterilization process including heating and purification steps. This may make it possible to provide a sterilizer for a fast and safe sterilization.

According to some embodiments of the inventive concept, a vacuum container is used to secure a volume of a vacuum pouch, unlike a conventional sterilization chamber. Accordingly, it is possible to reduce a volume of a small space required to perform a sterilization process on a vacuum pouch and consequently to reduce an amount of a sterilant to be used for the sterilization process.

DETAILED DESCRIPTION

Figure 1:
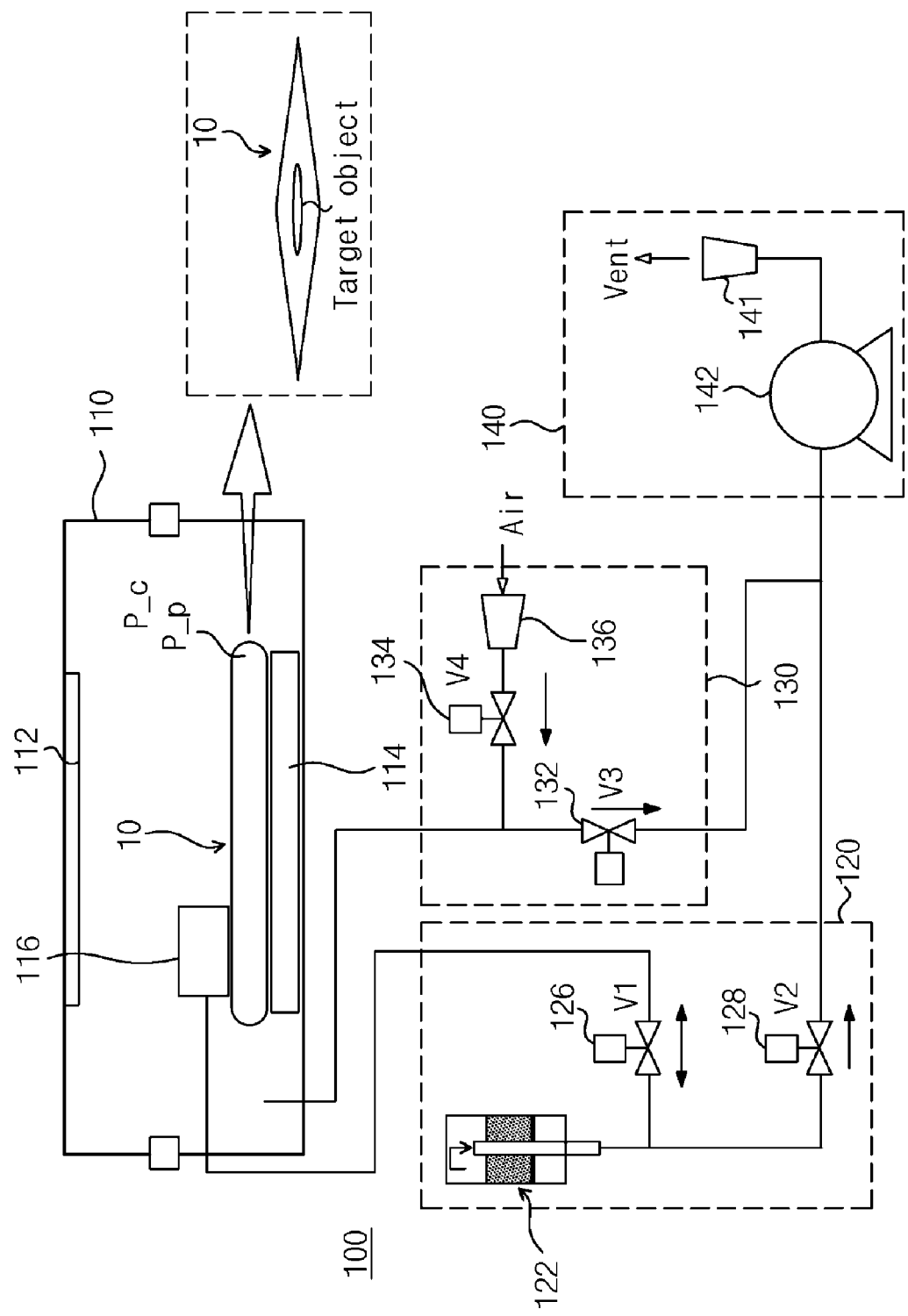
FIG. 1 is a schematic diagram illustrating a sterilization apparatus according to example embodiments of the inventive concept.

Generally, a chemical sterilization process using a sterilant may include disposing a wrapper with a target object in a sterilization chamber, and here the wrapper may include a selectively permeable film (e.g., TIVEK) that is permeable to the sterilant. If the sterilant is injected into the sterilization chamber, the sterilant may permeate the wrapper and sterilize the target object in the wrapper. In this sterilization method, efficiency of the sterilization may be rapidly lowered by an additional wrapper. Furthermore, for the wrapper, an additional long time purification process may be needed to remove the sterilant adsorbed in the sterilization process. Since the sterilant is injected into the sterilization chamber, a large amount of sterilant is used. The sterilant may cause environmental pollution. Also, an evacuating purification process may be performed, before evacuating the sterilant to the outside. The evacuating purification process may lead to deterioration in performance of a vacuum pump. Thus, it is necessary to develop a new sterilization method using a tiny amount of sterilant.

According to some embodiments of the inventive concept, to continue the sterilization process, a vacuum wrapper is used instead of the sterilization chamber. The vacuum wrapper may be directly sent to a user or may be used for long time storage, after the sterilization process is complete. In the case where the sterilant is injected into the vacuum wrapper, a volume defined by the vacuum wrapper may be much smaller than that in the conventional sterilization chamber. Accordingly, an amount of the sterilant used may be significantly reduced.

By evacuating air from the vacuum wrapper using a vacuum pump, the vacuum wrapper may have a vacuum pressure lower than the atmospheric pressure, and then, the sterilant may be injected into the vacuum wrapper. In the case where the vacuum wrapper is in an atmospheric pressure environment, the vacuum wrapper may be shrunken by a difference in pressure between inner and outer spaces, and thus, it may be difficult to secure a space for sterilant diffusion. To secure the space for the sterilant diffusion, the vacuum wrapper may be disposed in a vacuum container, whose pressure is lower than that of the vacuum wrapper. Accordingly, the vacuum wrapper may be expanded by low external pressure, thereby providing the space for the sterilant diffusion. This space may be used as a pathway allowing the sterilant to be diffused, and thus, it is possible to stably sterilize a target object such as lumen. The vacuum container may be used to control the external pressure of the vacuum wrapper, and an inner surface of the vacuum container may not be exposed to the sterilant. Thus, there may be no necessity to purify the air evacuated from the vacuum container. That is, only the sterilant injected into the vacuum wrapper may be evacuated and purified.

In the case where, after the sterilization process, the sterilant is evacuated from the vacuum wrapper, a fraction of the sterilant may remain in the vacuum wrapper. To effectively remove such a residual sterilant, the vacuum wrapper may include a dielectric barrier film, which is configured to perform a dielectric barrier discharge, and in which a ground layer, a dielectric layer, and a conductive layer with a hole array pattern are provided. In the case where a high voltage is applied between the ground layer and the conductive layer, a dielectric barrier discharge may occur in the vacuum wrapper. The dielectric barrier discharge may be used for a purification process of decomposing the sterilant to a non-hazardous gas. That is, the purification process using the dielectric barrier discharge may be performed in real time during the evacuating process and after the sterilization process.

According to some embodiments of the inventive concept, the dielectric barrier discharge may include heating a target object with or without an injected sterilant. If the vacuum wrapper is vacuumized, the convection-based heat transfer may be ineffective. The dielectric barrier discharge may be used to heat the target object to an optimized temperature for the sterilization process. The dielectric barrier discharge may be used to decompose gas to heated neutral particles, electrons, and ions. The heated neutral particle or the ion may be incident into the target object or the inner surface of the vacuum wrapper, and thus, its energy may be transferred to the target object and the vacuum wrapper. Also, the heating of the target object may evaporate water remaining in the target object. The presence of the water in the target object may lead to a reduction in efficiency of the sterilization process and may make it difficult to stably maintain the vacuum pressure.

In certain embodiments, for the dielectric barrier discharge, a process of supplying and activating the sterilant such as oxygen or ozone may be performed.

According to some embodiments of the inventive concept, the plasma discharge may be performed to increase temperature of a wrapping material, and then, the wrapping material may be maintained at a vacuum pressure that is lower than an external pressure. Accordingly, the wrapping material may be shrunken, and this may make it possible to effectively heat the target object by a direct heat conduction through the wrapping material.

According to some embodiments of the inventive concept, a sterilant may be directly injected into a vacuum wrapper, in which an impermeable film for a vacuum sealing is used, and in this case, owing to limitation of the space for the sterilant diffusion, it is possible to improve efficiency of the sterilization process. Furthermore, it is possible to overcome the user's safety issue, which may occur when the sterilant is absorbed in the vacuum wrapper or remains on an outer surface of the vacuum wrapper. In addition, since the vacuum wrapper is vacuum packaged, the vacuum wrapper may be used for long time storage in a sterile state. For example, the vacuum wrapper may be used to maintain its sterile state, even when the vacuum wrapper is provided within contamination, high-temperature, and high-humidity environment. A sterilant injection port or a connection member of the vacuum wrapper may be sealed in real time by a thermocompression process performed in the vacuum container.

According to some embodiments of the inventive concept, a vacuum container disposed outside the vacuum wrapper may be used to secure a volume of the vacuum wrapper or to provide the space for the sterilant diffusion, and thus, it is unnecessary to form a conduit such as an embossing pattern.

According to some embodiments of the inventive concept, in order to effectively diffuse the sterilant in the vacuum wrapper and supply the sterilant to the target article, it is necessary to secure the sufficient volume of the vacuum wrapper, after the direct supplying of the sterilant into the vacuum wrapper. To this end, the vacuum container disposed outside the vacuum wrapper may be used to perform the sterilization process.

According to some embodiments of the inventive concept, a polyethylene (PE) film may be used to seal the vacuum wrapper, in which the target object is contained, and to allow for the vacuumization of the vacuum wrapper and the direct sterilant supply through the sterilant injection port of the vacuum wrapper.

According to some embodiments of the inventive concept, the vacuum wrapper may be configured to include a film, in which an electrode for generating plasma is formed. In this case, by applying electric power to the vacuum wrapper, plasma may be produced in the vacuum wrapper, and the plasma may be used to effectively increase temperature of the target object and to purify the sterilant remaining in the vacuum wrapper after the sterilization process. Thus, it is possible to improve efficiency of the sterilization process and secure the user's safety.

According to some embodiments of the inventive concept, the vacuum wrapper may be configured to have a laminate film structure including a dielectric barrier layer, a patterned metal electrode attached to a surface of the dielectric barrier layer, and a ground electrode attached to an opposite surface of the dielectric barrier layer. Electric power may be applied to the vacuum wrapper to produce plasma through the dielectric barrier discharge. The plasma may be used for the heating and purification processes.

Hereinafter, example embodiments of the inventive concept will be described in detail with reference to the accompanying drawings. The advantages and features of the inventive concept and the method of achieving them will now be described more fully with reference to the accompanying drawings, in which example embodiments are shown. Example embodiments of the inventive concept may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. the inventive concept is only defined by the claims.

Like reference numerals refer to like elements throughout the specification. Therefore, although the same reference numerals or similar reference numerals are not mentioned or described in the drawings, they may be described with reference to other drawings. Further, even if the reference numerals are not shown, they may be described with reference to other drawings.

FIG. 1 is a schematic diagram illustrating a sterilization apparatus according to example embodiments of the inventive concept.

Figure 2:
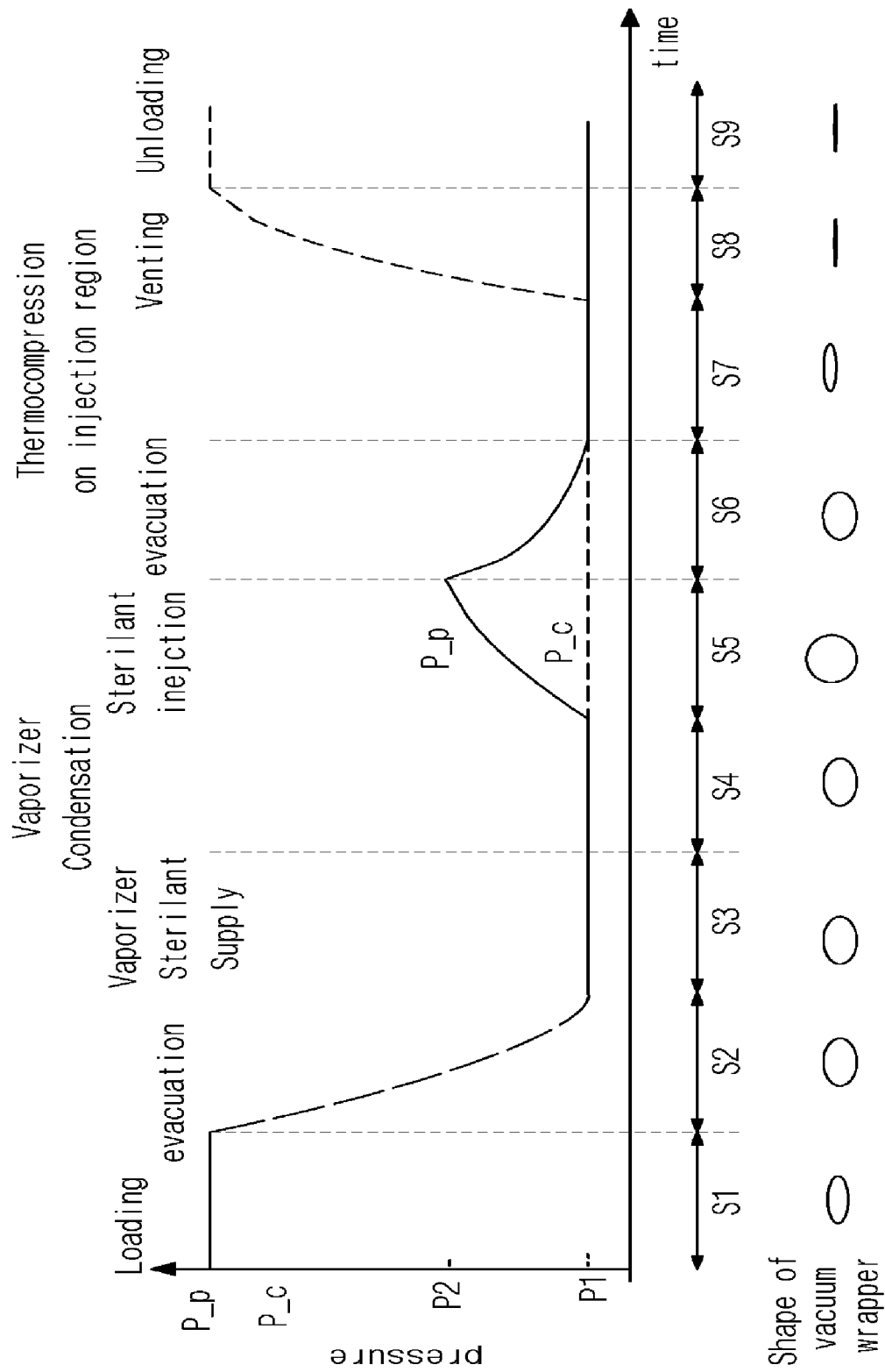
FIG. 2 is a diagram illustrating an example of a sterilization process which is performed using the sterilization apparatus of FIG. 1.

FIG. 2 is a diagram illustrating an example of a sterilization process which is performed using the sterilization apparatus of FIG. 1.

Figure 3A:
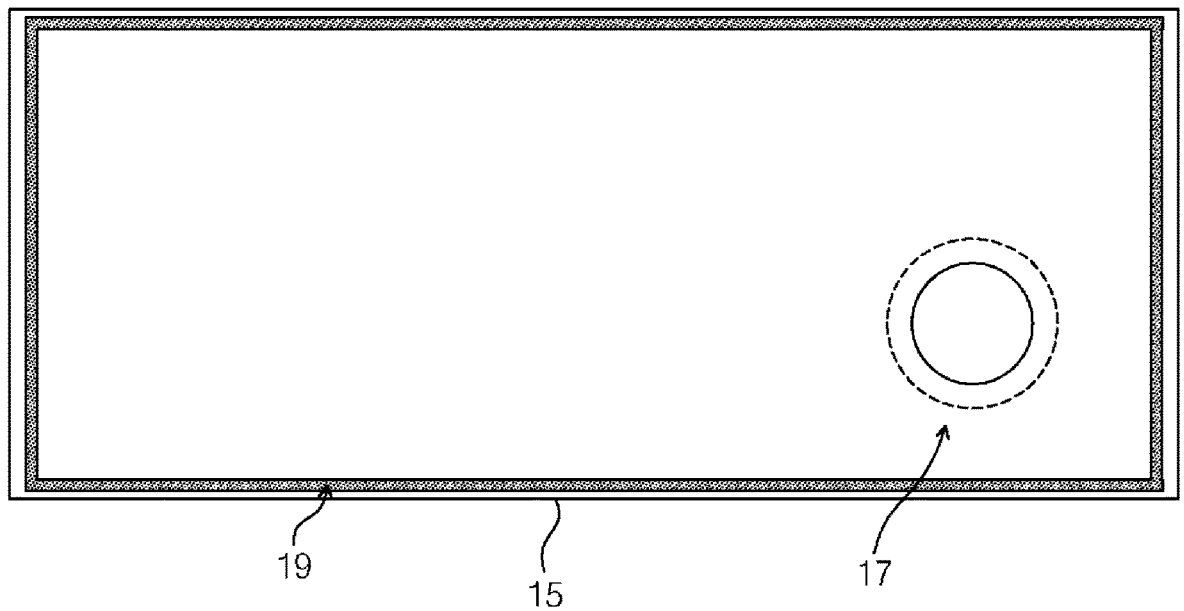
FIGS. 3A to 3C are plan views illustrating a vacuum wrapper and upper and lower films thereof.
Figure 3B:
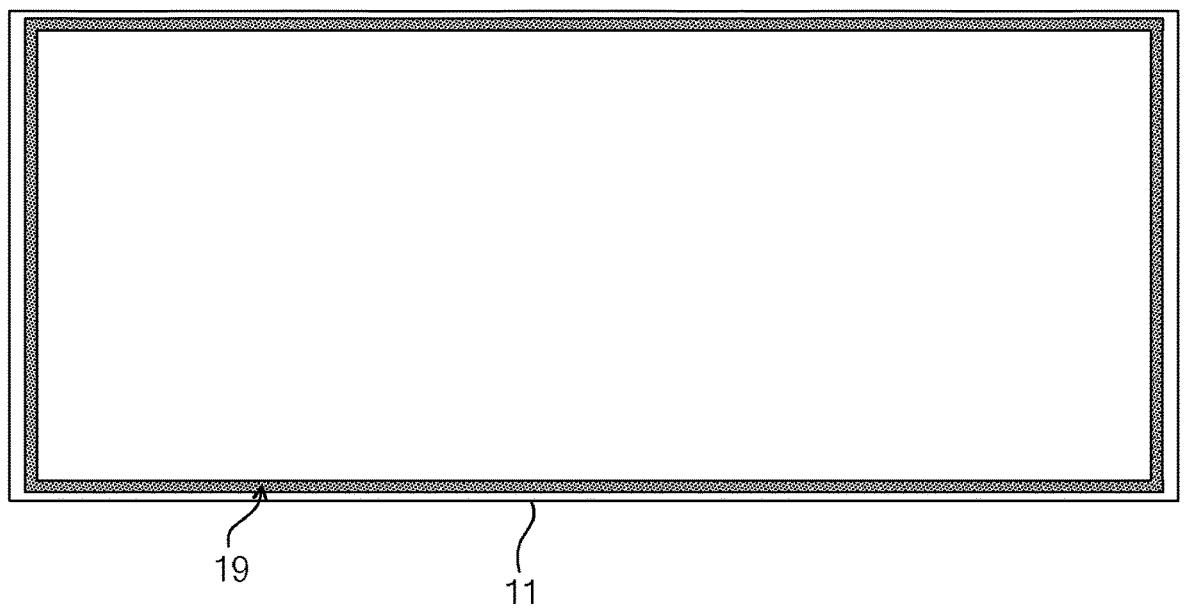
Figure 3C:
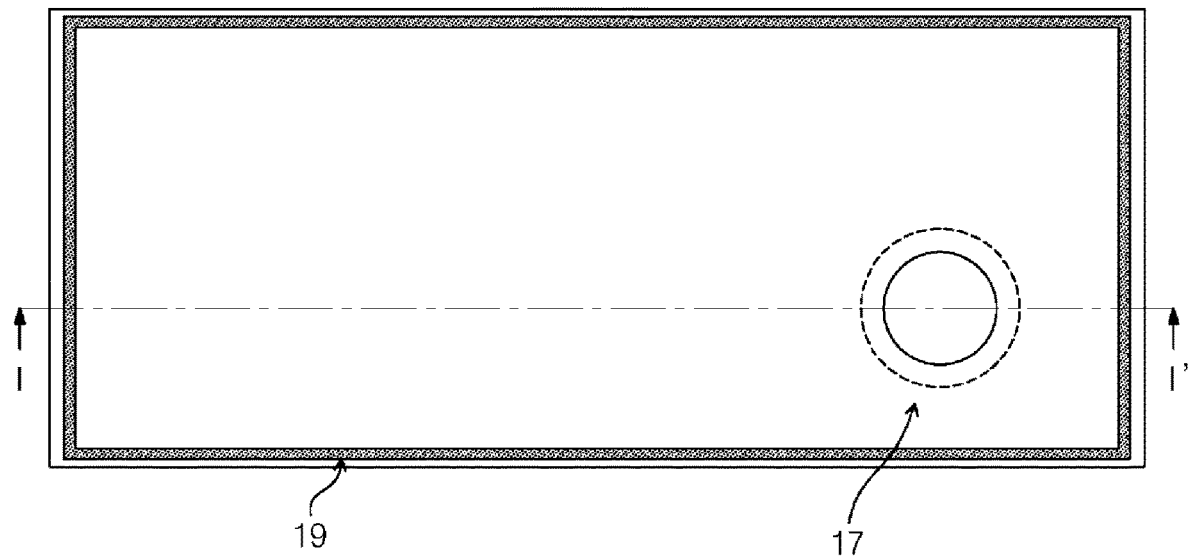

FIGS. 3A to 3C are plan views illustrating a vacuum wrapper and upper and lower films thereof.

Figure 3D:
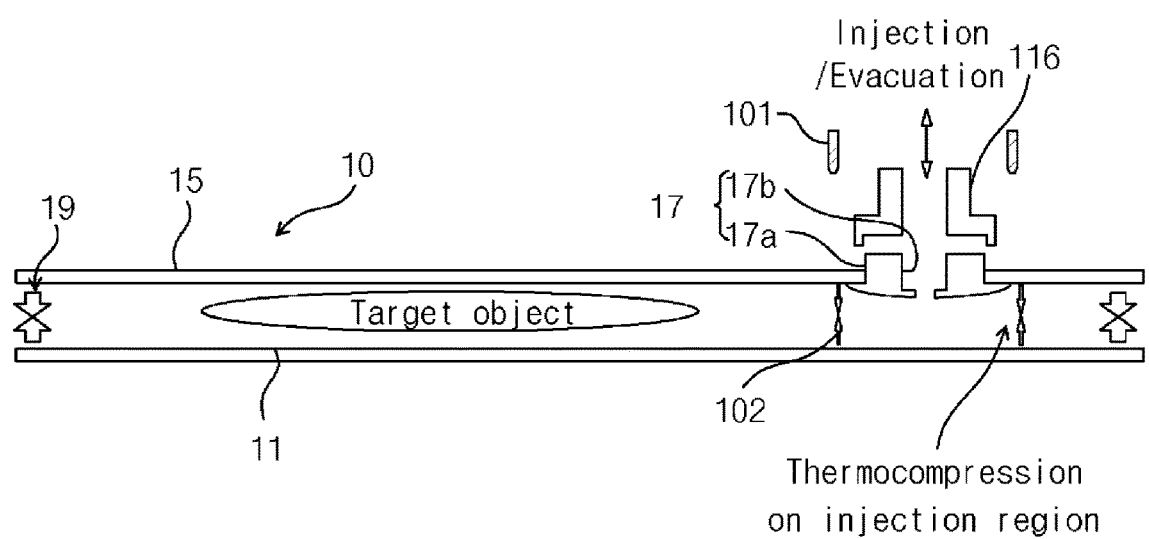
FIG. 3D is a sectional view of the vacuum wrapper, taken along line I-I' of FIG. 3C.

FIG. 3D is a sectional view of the vacuum wrapper, taken along line I-I' of FIG. 3C.

Referring to FIGS. 1 to 3, a sterilization apparatus 100 may include a vacuum container 110, a vacuum wrapper 10, a vacuum pump 140, a sterilant providing part 120, and an air injection part 130. Here, the vacuum wrapper 10 may be loaded in the vacuum container 110 and may be used to store and seal a target object, and the vacuum pump 140 may be configured to evacuate the air from the vacuum container 110 and the vacuum wrapper 10. The sterilant providing part 120 may be configured to inject a sterilant into the vacuum wrapper 10, and the air injection part 130 may be configured to inject the air into the vacuum container 110. When the injection of the sterilant into the vacuum wrapper 10 is finished, the vacuum container 110 may be maintained at a vacuum state of a base pressure P1 and the pressure of the vacuum wrapper 10 may be higher than the base pressure P1.

The vacuum container 110 may be a metal chamber with a fixed shape. The vacuum container 110 may include a door (not shown), which is used to load the vacuum wrapper 10, a lower heater 114, which is disposed in the vacuum container 110 and is used to heat the vacuum wrapper 10, and an upper heater 112, which is used to heat the vacuum container 110.

The door may be provided through a top or side wall of the vacuum container 110. The lower heater 114 may be used to load the vacuum wrapper 10 thereon. The lower heater 114 may be used to heat the vacuum wrapper 10 to the temperature of about 60° C. The upper heater 112 may be provided on the top wall of the vacuum container 110 and may be used to heat the vacuum container to the temperature of about 60° C.

The sterilant providing part 120 may include a vaporizer 122, which is used to heat and evaporate a sterilant supplied from the outside, a first valve 126, which is disposed between an output terminal of the vaporizer 122 and a connection member 17 of the vacuum wrapper 10, and a second valve 128, which is disposed between the output terminal of the vaporizer 122 and an input terminal of the vacuum pump 140.

The vaporizer 122 may be configured in such a way that a liquid sterilant is supplied into the vaporizer 122 through a constant injection device (not shown). In the case where the sterilant is hydrogen peroxide, the vaporizer 122 may be heated to the temperature of about 70° C.-100° C. The liquid sterilant may be evaporated. The sterilant evaporated through the output terminal of the vaporizer 122 may be injected into the vacuum wrapper 10 through the first valve 126. The vacuum wrapper 10 may include a connection member 17, which is configured to allow the sterilant to be supplied into the vacuum wrapper 10 and to evacuate gas from an inner space of the vacuum wrapper. The coupling member 116, which is coupled to the connection member 17, may be disposed in the vacuum container 110. The coupling member 116 may be coupled to the connection member 17 by a one-touch fitting method.

The second valve 128 may be disposed between the output terminal of the vaporizer 122 and the input terminal of the vacuum pump 140. In the case where the second valve 128 is opened and the first valve 126 is closed, a fraction of the sterilant evaporated by the vaporizer 122 may be evacuated to the outside through the vacuum pump 140. In the case where a liquid hydrogen peroxide sterilant is supplied into the vaporizer, this process may be used in a concentration process of removing evaporated water molecules and thereby increasing a concentration of the sterilant.

The air injection part 130 may include an air filter 136, which is used to filter the air provided from the outside, a third valve 132, which is disposed between an input/output terminal of the vacuum container 110 and the input terminal of the vacuum pump 140, and a fourth valve 134, which is disposed between the air filter 136 and the input/output terminal of the vacuum container 110.

The air filter 136 may be a high efficiency particulate air filter (HEPA) filter capable of removing particles and germs from the external air. The fourth valve 134 may be used to supply the air into the vacuum container 110 through the input/output terminal of the vacuum container 110 and thereby to increase the pressure of the vacuum container 110. The third valve 132 may be provided between the input/output terminal of the vacuum container 110 and the input terminal of the vacuum pump 140. In the case where the third valve 132 is opened and other valves are closed, the vacuum pump 140 may be used to evacuate gas from the vacuum container 110 through the input/output terminal of the vacuum container 110 and thereby to reduce the pressure of the vacuum container 110 to the base pressure P1. The base pressure P1 may be lower than several tens Torr.

The vacuum pump 140 may be used to evacuate the vacuum container 110 through the third valve 132 and evacuate the vacuum wrapper 10 through the first and second valves 126 and 128. The vacuum pump 140 may include a rotary pump 142 and a mist trap 141.

The vacuum wrapper 10 may include the connection member 17, which is configured to allow the sterilant to be supplied into the vacuum wrapper 10 and to evacuate gas from an inner space of the vacuum wrapper 10. The connection member 17 may be thermocompressed to the vacuum wrapper 10 and may include a penetration hole 17b. A portion 102 adjacent to the connection member 17 may be thermocompressed after the process of evacuating the sterilant is finished. In some embodiments, the vacuum wrapper 10 may be formed of or include polyethylene which can be easily sealed by the thermocompression method. In certain embodiments, the vacuum wrapper 10 may be formed of or include at least one of various plastic materials which can be easily sealed by the thermocompression method.

When a target object is disposed in the vacuum wrapper 10, the vacuum wrapper 10 may be vacuum-sealed by the thermocompression method. The vacuum wrapper 10 may be formed of an impermeable material capable of preventing the external gas from permeating through the vacuum wrapper 10. For example, the vacuum wrapper 10 may be formed of polyethylene. The vacuum wrapper 10 may include a lower film 11 and an upper film 15. The lower and upper films 11 and 15 may be used to provide an internal space of the vacuum wrapper 10 through a border thermocompression 19.

The vacuum wrapper 10 may include the connection member 17, which is formed in the vacuum wrapper 10 by the thermocompression method. In the vacuum container 110, the connection member 17 may be used as a pathway allowing the sterilant to be supplied into the vacuum wrapper 10 through the coupling member 116 and to be evacuated from the vacuum wrapper 10.

The connection member 17 may be coupled to the coupling member 116 in the vacuum container 110, and after the process of evacuating the sterilant, the thermocompressed portion may be formed near the connection member 17 in the vacuum container 110 by the thermocompression method. The thermocompressed portion may be formed using a thermocompression device 101 provided in the vacuum container 110.

The connection member 17 may be used to vacuumize an internal space of the vacuum wrapper 10 or to supply a sterilant into the vacuum wrapper 10. The connection member 17 may be inserted into an opening, which is formed through a surface of the vacuum wrapper 10, and may be fastened to the vacuum wrapper 10 by the thermocompression method. In the vacuum container 110, the connection member 17 may be coupled to the coupling member 116 and may be used as a pathway for evacuating and supplying the sterilant from and to the vacuum wrapper 10. After the sterilization process, a thermocompression method may be performed at a vacuum state to seal the lower and upper films 11 and 15 near the connection member 17. Accordingly, the vacuum wrapper 10 may be vacuum-packed.

In certain embodiments, the connection member 17 may include a connection member for vacuumizing the vacuum wrapper 10 and other connection member for supplying the sterilant.

Hereinafter, a sterilization process using the sterilization apparatus will be described.

A sterilization method may include loading a vacuum wrapper 10, which contains and seals a target object, in the vacuum container 110 (in S1), evacuating the vacuum container 110 and the vacuum wrapper 10 (in S2), injecting a sterilant into the vacuum wrapper 10, which is disposed in the vacuum container 110 and is maintained at a vacuum state (in S5), and venting the vacuum container 110 to allow it to have the atmospheric pressure (in S8). The vacuum wrapper 10 may be formed of a material preventing an external gas from permeating into the vacuum wrapper 10.

As an example, the target object may be a medical apparatus. The target object may be disposed in the vacuum wrapper 10, and then, a border region 19 of the vacuum wrapper 10 may be sealed by a thermocompression method. The sealed vacuum wrapper 10 may be loaded in the vacuum container 110, and the vacuum container 110 may be sealed (in S1). In this case, since there is no difference in pressure between inner and outer spaces, the vacuum wrapper 10 may have a constant volume. The vacuum wrapper 10 may be heated up to the temperature of 50° C.-65° C. by a heater provided in the vacuum container 110.

Thereafter, the vacuum container 110 and the vacuum wrapper 10 may be evacuated (in S2). The vacuum container 110 may be evacuated to have a base pressure, and the vacuum wrapper 10 may be evacuated to have a pressure lower than the atmospheric pressure. The fourth valve 134 may be closed, and the first to third valves 126, 128, and 132 may be opened. The vacuum wrapper 10 may include the connection member 17, which is used to inject the sterilant into the vacuum wrapper 10 or to evacuate an internal gas from the vacuum wrapper 10. The vacuum container 110 and the vacuum wrapper 10 may be evacuated at the same time. The pressure of the vacuum container 110 may be substantially equal to or slightly lower than that of the vacuum wrapper 10. In this case, since there is substantially no difference in pressure between inner and outer spaces of the vacuum wrapper 10, the vacuum wrapper 10 may have a constant volume. In the case where the pressures of the vacuum container 110 and the vacuum wrapper 10 reach a desired value, the first to third valves 126, 128, and 132 may be closed.

Next, a liquid sterilant may be supplied into the vaporizer 122 (in S3). The sterilant may be hydrogen peroxide. The vaporizer 122 may be heated up to the temperature of about 70° C.-100° C. Thus, the water contained in the supplied sterilant may be evaporated in advance.

In certain embodiments, the pressure of the vacuum container 110 may be maintained to a level higher than that of the vacuum wrapper 10, and this may allow heat of the heated wrapping material to be more efficiently transferred to the target object. Here, the third valve 132 connected to the vacuum container 110 may be closed and the fourth valve 134 may be opened, and thus, the pressure of the vacuum container 110 may be increased by an external air injected into the vacuum container 110.

Thereafter, a vaporizer condensation process may be performed (in S4). A liquid hydrogen peroxide supplied from the outside may have a concentration of 50 weight percent or less. The vaporizer condensation process may be performed to increase the concentration of the hydrogen peroxide. For example, the second valve 128 may be opened to evacuate the water steam evaporated in the vaporizer 122 to the outside through the vacuum pump 140. As a result of the condensation process, the concentration of the hydrogen peroxide may be increased to 70 weight percent or higher. The higher the concentration of the hydrogen peroxide, the less a process time for the sterilization. In some embodiments, the sterilant may be hydrogen peroxide whose concentration is 50 weight percent or higher.

Next, the condensed sterilant may be injected into the vacuum wrapper 10. For example, if the second valve 128 is closed and the first valve 126 is opened, the sterilant evaporated in the vaporizer 122 may be injected into the vacuum wrapper 10 (in S5). If the sterilant is injected into the vacuum wrapper 10, the vacuum wrapper 10 may have a pressure P2 that is higher than the base pressure of the vacuum container 110. For example, the pressure P2 of the vacuum wrapper 10 may range from several Torr to several tens Torr. In this case, owing to the difference in pressure between the inner and outer spaces of the vacuum wrapper 10, the vacuum wrapper 10 may be expanded to have a sufficient volume for the diffusion of sterilant. The vaporized sterilant may be used to sterilize the target object. When the injection of the sterilant is finished, the pressure of the vacuum wrapper 10 may be about several tens Torr. If a predetermined amount of the sterilant is injected into the vacuum wrapper 10, the first valve 126 may be closed.

Thereafter, the sterilant in the vacuum wrapper 10 may be evacuated (in S6). In the case where the sterilant is evacuated from the vacuum wrapper 10, the pressure of the vacuum wrapper 10 may become equal to the base pressure of the vacuum container 110. To this end, the first valve 126 and the second valve 128 may be opened. The sterilant in the vacuum wrapper 10 may be evacuated to the outside through the vacuum pump 140. In this case, the pressure of the vacuum wrapper 10 may be decreased to a level similar to the base pressure of the vacuum container 110. Accordingly, there may be substantially no difference in pressure between the inner and outer spaces of the vacuum wrapper 10, and thus, the vacuum wrapper 10 may be shrunken. If the step of evacuating the sterilant from the vacuum wrapper 10 is finished, the first valve 126 and the second valve 128 may be closed.

Next, in the vacuum container 110, a portion 102 of the vacuum wrapper 10 adjacent to the connection member 17 may be sealed by a thermocompression method (in S7). In some embodiments, the thermocompression method may be performed to seal the vacuum wrapper 10, in which the target object is disposed. The vacuum wrapper 10 may be hermetically sealed, when the sterilant and the air are evacuated from the vacuum wrapper 10.

Thereafter, an external air may be injected into the vacuum container 110 until the pressure of the vacuum container 110 reaches the atmospheric pressure (in S8). For example, the first to third valves 126, 128, and 132 may be closed and the fourth valve 134 may be opened. Accordingly, the external air may flow into the vacuum container 110. As the pressure of the vacuum container 110 approaches the atmospheric pressure, the vacuum wrapper 10 may be compressed by the pressure difference.

In certain embodiments, when the external air is injected into the vacuum container 110, the external air may also be injected into the vacuum wrapper 10. In this case, there may be substantially no difference in pressure between the inner and outer spaces of the vacuum wrapper 10, and thus, the vacuum wrapper 10 may be maintained to a constant volume under the atmospheric pressure. In the case where the vacuum wrapper 10 has a low internal pressure and is thus shrunken under the atmospheric pressure environment, the pressure difference may lead to damage of the target object disposed in the vacuum wrapper 10. To avoid this problem, when the venting step is performed on the vacuum container 110, the vacuum container 110 may be vented to allow it to have the atmospheric pressure.

Next, the vacuum wrapper 10 may be unloaded from the vacuum container 110 (in S9).

In the sterilization method according to some embodiments of the inventive concept, in order to secure a space for the sterilant diffusion in the vacuum wrapper 10, the vacuum wrapper 10 may be evacuated in the vacuum container 110, a sterilant may be supplied into the vacuum wrapper 10, and the sterilant may be evacuated from the vacuum wrapper 10.

Furthermore, if the sterilant is supplied into the vacuum wrapper 10, the vacuum wrapper 10 may have a pressure that is higher than that of the vacuum container 110. In this case, owing to a small sterilization space, it is possible to improve efficiency of the sterilization process and reduce an amount of the sterilant used. In addition, since the outer film of the vacuum wrapper 10 is not contaminated by the sterilant, the user's safety can be improved. The vacuum wrapper 10 may be used for long time storage, compared with the conventional permeable wrapper.

Figure 4:
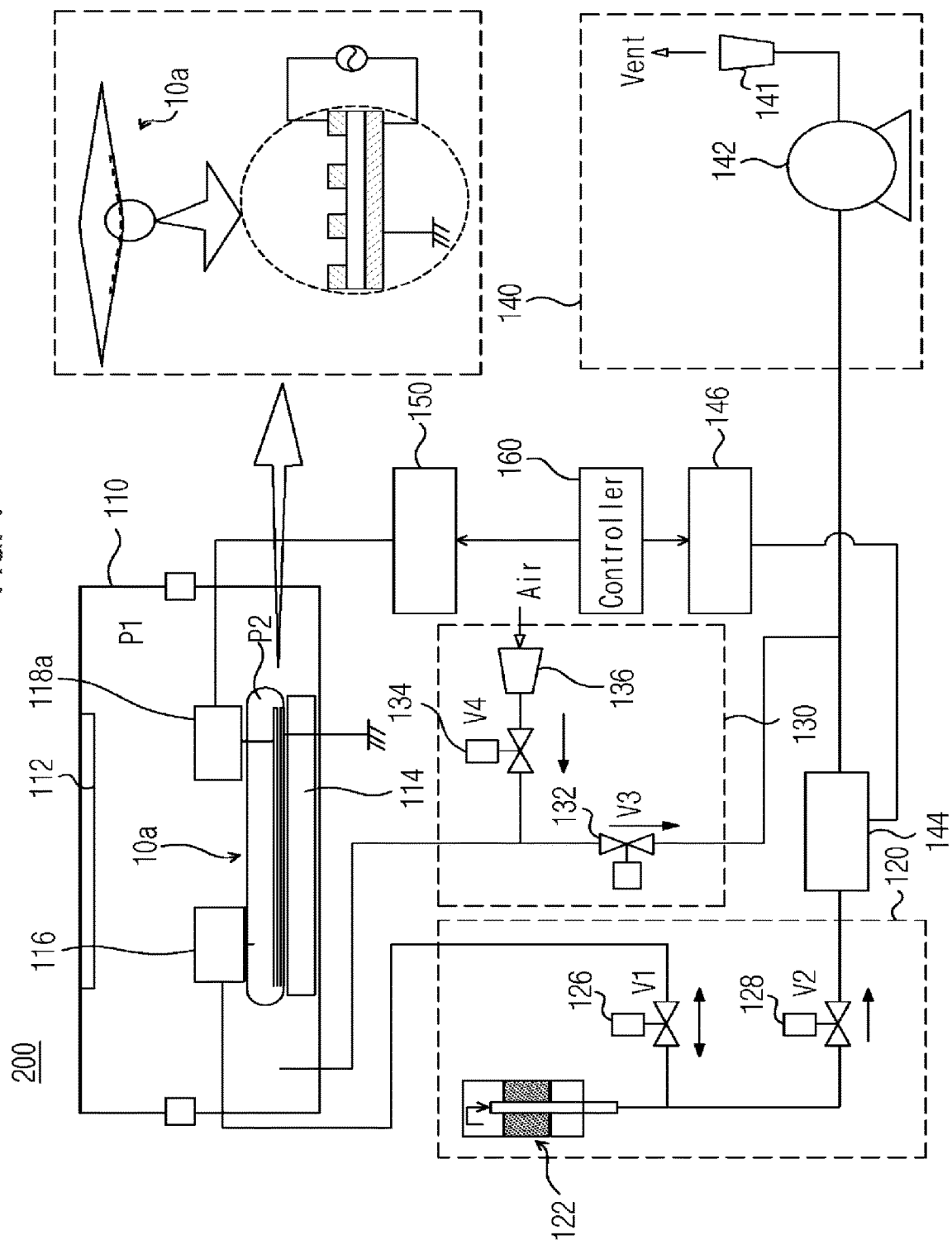
FIG. 4 is a schematic diagram illustrating a sterilization apparatus according to other embodiments of the inventive concept.

FIG. 4 is a schematic diagram illustrating a sterilization apparatus according to other embodiments of the inventive concept.

Figure 5:
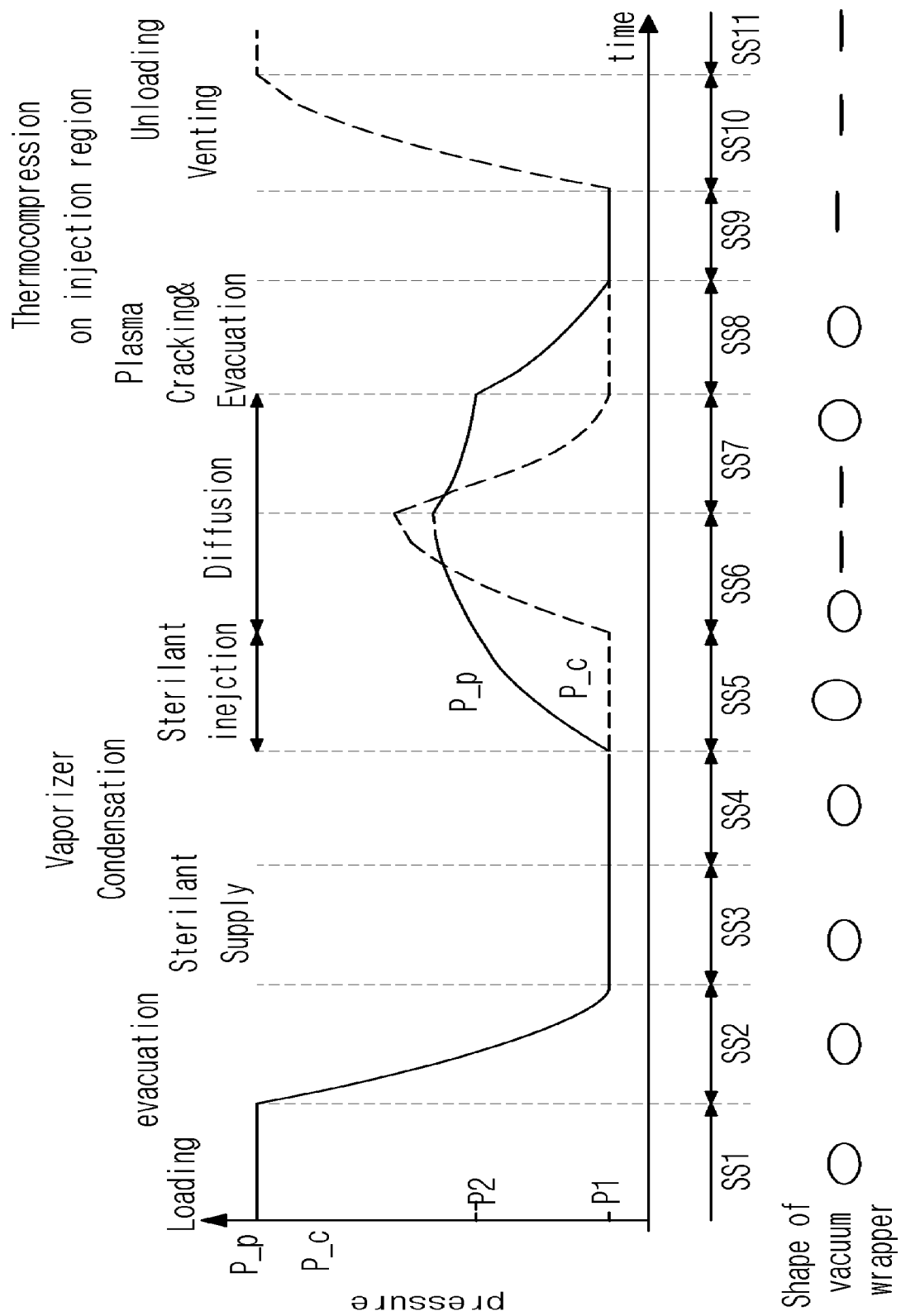
FIG. 5 is a diagram illustrating an example of a sterilization process which is performed using the sterilization apparatus of FIG. 4.

FIG. 5 is a diagram illustrating an example of a sterilization process which is performed using the sterilization apparatus of FIG. 4.

Figure 6A:
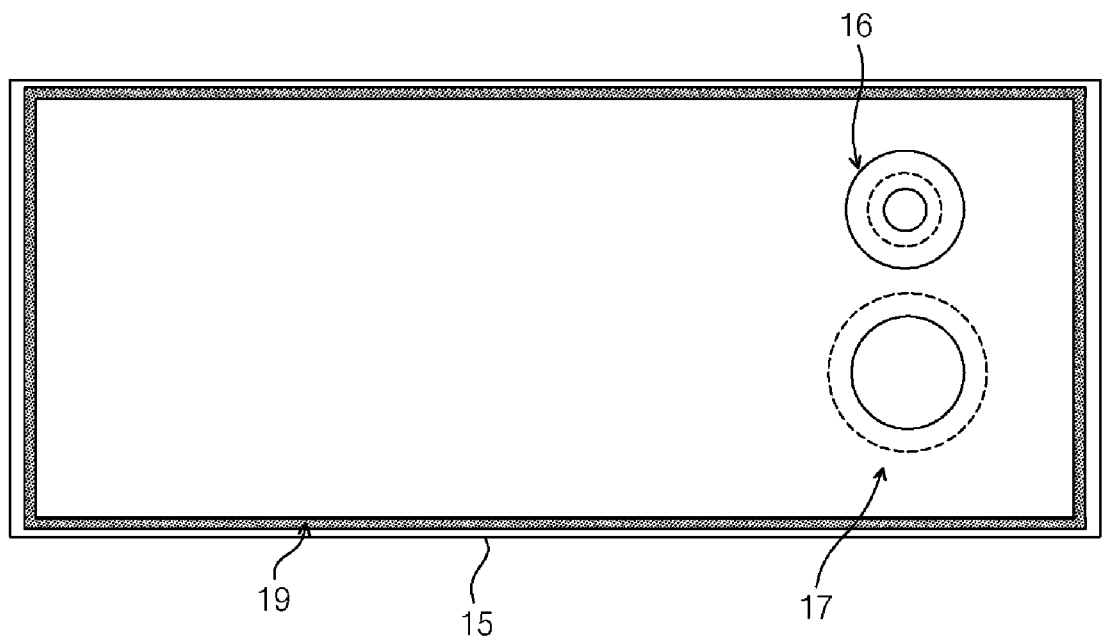
FIGS. 6A to 6C are plan views illustrating a vacuum wrapper and upper and lower films thereof.
Figure 6B:
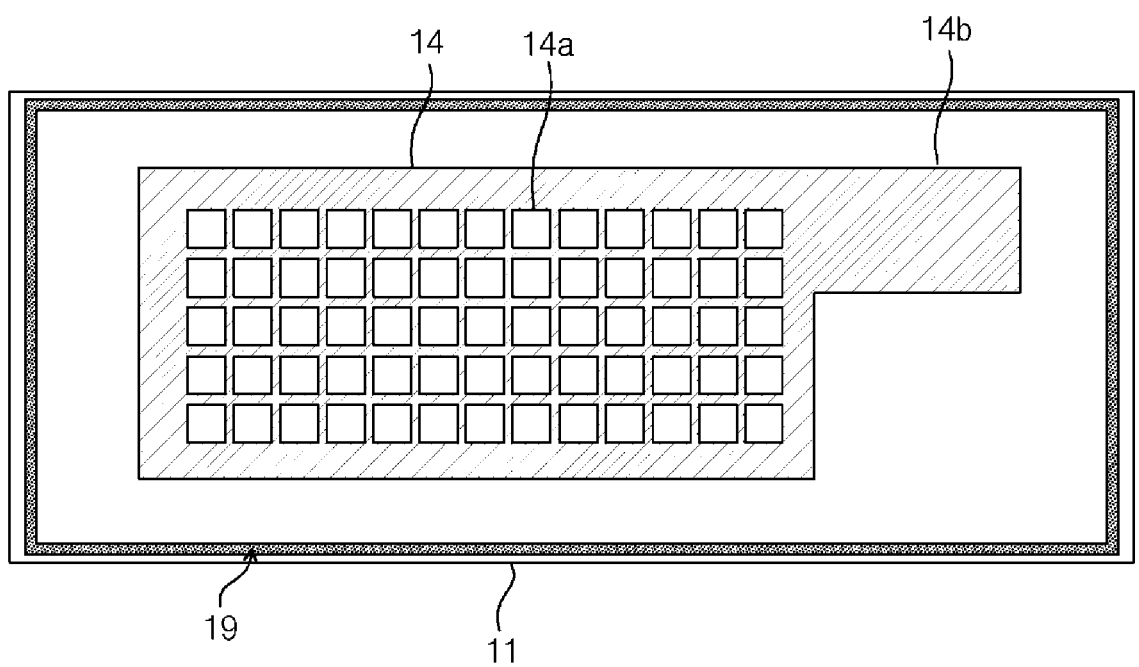
Figure 6C:
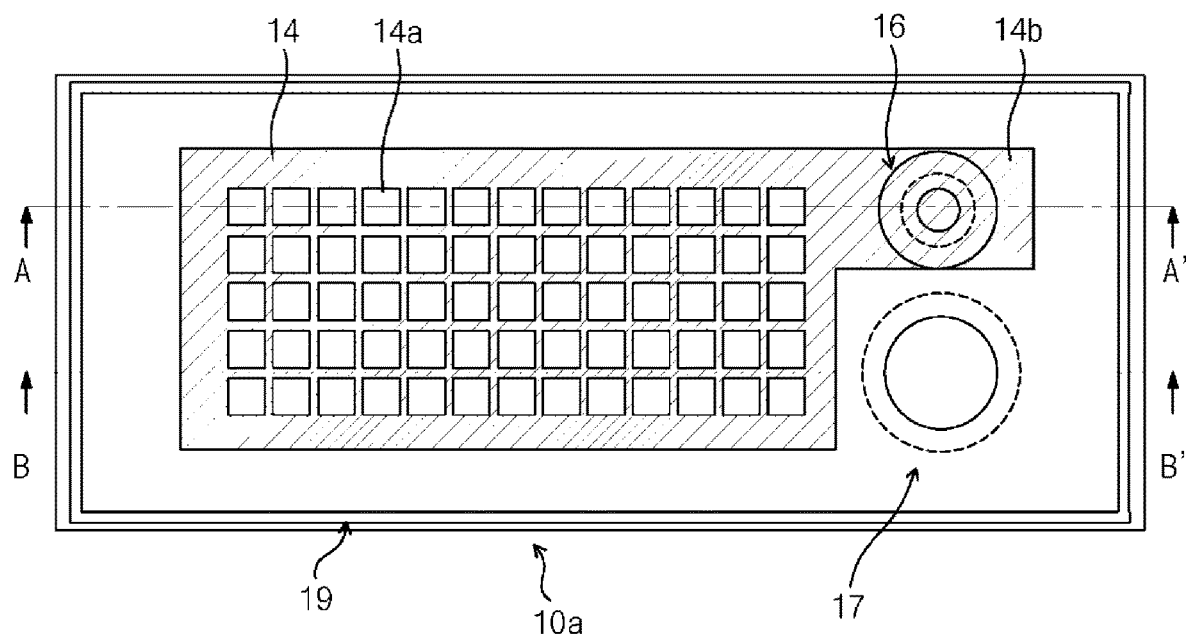

FIGS. 6A to 6C are plan views illustrating a vacuum wrapper and upper and lower films thereof.

Figure 6D:
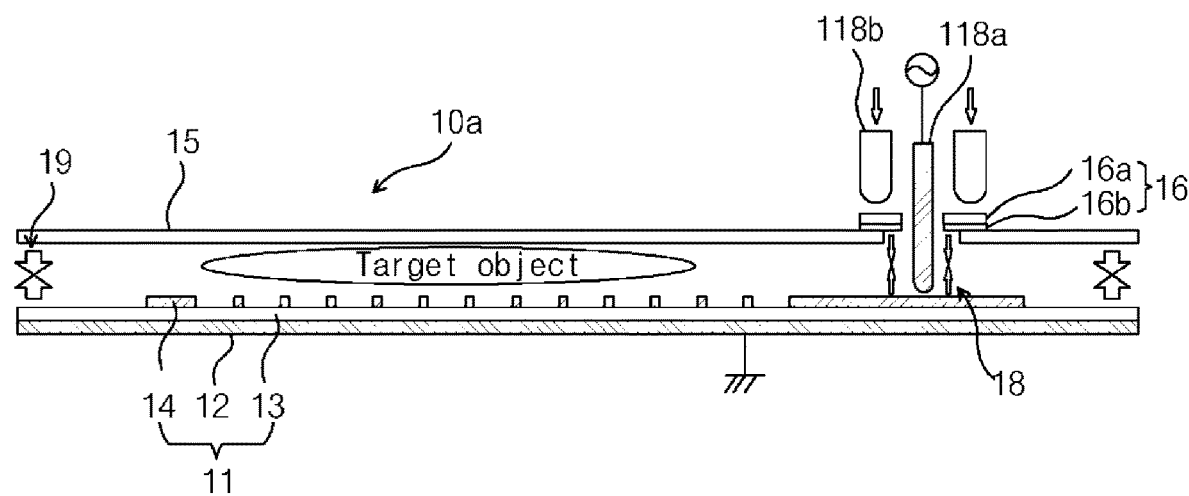
FIG. 6D is a sectional view of the vacuum wrapper, taken along line A-A' of FIG. 6C.

FIG. 6D is a sectional view of the vacuum wrapper, taken along line A-A' of FIG. 6C.

Figure 6E:
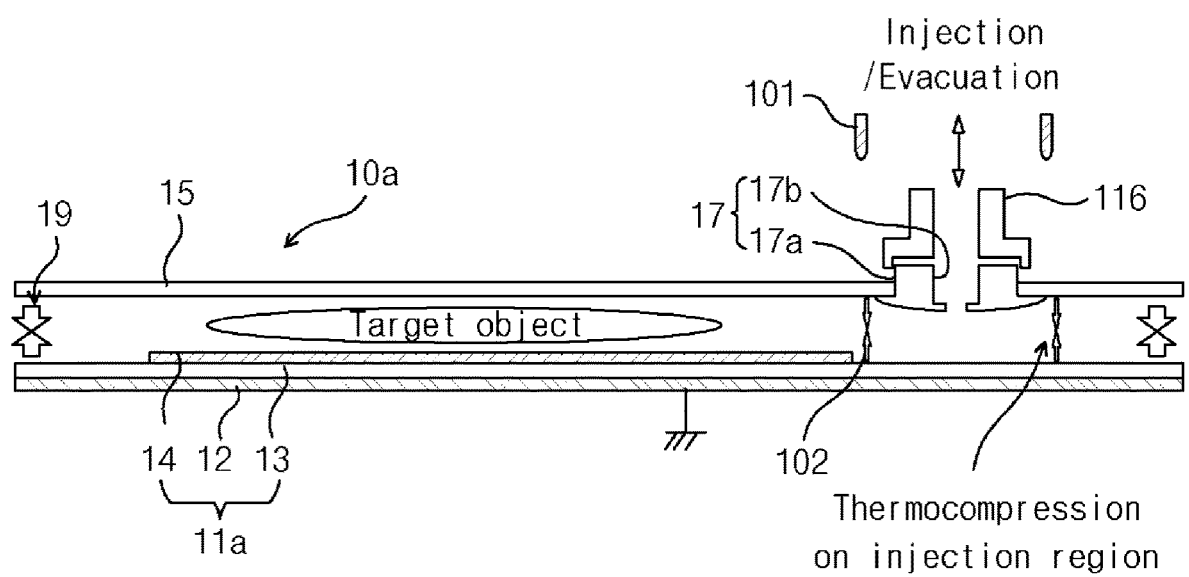
FIG. 6E is a sectional view of the vacuum wrapper, taken along line B-B' of FIG. 6C.

FIG. 6E is a sectional view of the vacuum wrapper, taken along line B-B' of FIG. 6C.

Referring to FIGS. 4, 5, and 6A to 6E, a sterilization apparatus 200 may include a vacuum container 110, a vacuum wrapper 10a, a vacuum pump 140, a sterilant providing part 120, and an air injection part 130. Here, the vacuum wrapper 10a may be loaded in the vacuum container 110 and may be used to store and seal a target object, and the vacuum pump 140 may be configured to evacuate the air from the vacuum container 110 and the vacuum wrapper 10a. The sterilant providing part 120 may be configured to inject a sterilant into the vacuum wrapper 10a, and the air injection part 130 may be configured to inject the air into the vacuum container 110. When the injection of the sterilant into the vacuum wrapper 10a is finished, the vacuum container 110 may be maintained at a vacuum state of a base pressure P1 and the pressure of the vacuum wrapper 10a may be higher than the base pressure P1.

The vacuum container 110 may be a metal chamber with a fixed shape. The vacuum container 110 may include a door (not shown), which is used to load the vacuum wrapper 10a, a lower heater 114, which is disposed in the vacuum container 110 and is used to load and heat the vacuum wrapper 10a, and an upper heater 112, which is used to heat the vacuum container 110.

The door may be provided through a top or side wall of the vacuum container 110. The lower heater 114 may be used to load the vacuum wrapper 10a thereon. The lower heater 114 may be used to heat the vacuum wrapper 10a to the temperature of about 60° C. The upper heater 112 may be provided on the top wall of the vacuum container 110 and may be used to heat the vacuum container 110 to the temperature of about 60° C.

The sterilant providing part 120 may include a vaporizer 122, which is used to heat and evaporate a sterilant supplied from the outside, a first valve 126, which is disposed between an output terminal of the vaporizer 122 and a connection member 17 of the vacuum wrapper 10a, and a second valve 128, which is disposed between the output terminal of the vaporizer 122 and an input terminal of the vacuum pump 140.

The vaporizer 122 may be configured in such a way that a liquid sterilant is supplied into the vaporizer 122 through a constant injection device (not shown). In the case where the sterilant is hydrogen peroxide, the vaporizer 122 may be heated to the temperature of about 70° C.-100° C. The liquid sterilant may be evaporated. The sterilant evaporated through the output terminal of the vaporizer 122 may be injected into the vacuum wrapper 10a through the first valve 126. The vacuum wrapper 10a may include the connection member 17, which is used to supply the sterilant from the outside to the vacuum wrapper 10a and to evacuate gas from an inner space of the vacuum wrapper 10a. The coupling member 116, which is coupled to the connection member 17, may be disposed in the vacuum container 110. The coupling member 116 may be coupled to the connection member 17 by a one-touch fitting method.

The second valve 128 may be disposed between the output terminal of the vaporizer 122 and the input terminal of the vacuum pump 140. In the case where the second valve 128 is opened and the first valve 126 is closed, a fraction of the sterilant evaporated by the vaporizer 122 may be evacuated to the outside through the vacuum pump 140. In the case where a liquid hydrogen peroxide sterilant is supplied into the vaporizer, this process may be used in a concentration process of removing evaporated water molecules and thereby increasing a concentration of the sterilant.

The air injection part 130 may include an air filter 136, which is used to filter the air provided from the outside, a third valve 132, which is disposed between an input/output terminal of the vacuum container 110 and the input terminal of the vacuum pump 140, and a fourth valve 134, which is disposed between the air filter 136 and the input/output terminal of the vacuum container 110.

The air filter 136 may be a high efficiency particulate air filter (HEPA) filter capable of removing particles and germs from the external air. The fourth valve 134 may be used to supply the air into the vacuum container 110 through the input/output terminal of the vacuum container 110 and thereby to increase the pressure of the vacuum container 110. The third valve 132 may be provided between the input/output terminal of the vacuum container 110 and the input terminal of the vacuum pump 140. In the case where the third valve 132 is opened and other valves are closed, the vacuum pump 140 may be used to evacuate gas from the vacuum container 110 through the input/output terminal of the vacuum container 110 and thereby to decrease the pressure of the vacuum container 110 to the base pressure P1. The base pressure P1 may be lower than several tens Torr.

The vacuum pump 140 may be used to evacuate the vacuum container 110 through the third valve 132 and evacuate the vacuum wrapper 10a through the first and second valves 126 and 128. The vacuum pump 140 may include a rotary pump 142 and a mist trap 141.

The vacuum wrapper 10a may include the connection member 17, which is used to supply the sterilant into the vacuum wrapper 10a and to evacuate gas from an inner space of the vacuum wrapper 10a. The connection member 17 may be thermocompressed to the vacuum wrapper 10a and may include a penetration hole 17b. A portion 102 adjacent to the connection member 17 may be thermocompressed after the process of evacuating the sterilant is finished. The thermocompressed portion 102 may be formed using a thermocompression device 101 provided in the vacuum container 110. The thermocompression device 101 may be lowered in the vacuum container 110 to perform a thermocompression process. In some embodiments, the vacuum wrapper 10a may be formed of or include polyethylene which can be easily sealed by the thermocompression method. In certain embodiments, the vacuum wrapper 10a may be formed of or include at least one of various plastic materials which can be easily sealed by the thermocompression method.

When a target object is disposed in the vacuum wrapper 10a, the vacuum wrapper 10a may be vacuum-sealed by the border thermocompression method. The vacuum wrapper 10a may be formed of an impermeable material capable of preventing the external gas from permeating through the vacuum wrapper 10a. For example, the vacuum wrapper 10a may be formed of polyethylene. The vacuum wrapper 10a may include a lower film 11a and an upper film 15, and the lower and upper films 11a and 15 may be used to provide an internal space of the vacuum wrapper 10a through a border thermocompression 19.

The lower film 11a of the vacuum wrapper 10a may include a ground layer 12, a dielectric layer 13, and a conductive layer 14 with a hole array pattern, which are sequentially stacked. The ground layer 12 may be used as an outer film of the vacuum wrapper 10a, and the conductive layer 14 may be used as an inner film of the vacuum wrapper 10a. The conductive layer 14 may include a discharge region 14a, in which a hole array pattern is provided, and a pad region 14b extending from the discharge region 14a.

The upper film 15 may include an opening which is formed to face the pad region 14b. The adhesive film 16 may be provided to be aligned with the opening. The adhesive film 16 may include an adhesive layer 16b. The adhesive film 16 may be provided in the form of a washer exposing the pad region 14b. A portion of the adhesive film 16 may be in contact with the upper film 15 adjacent to the opening, thereby sealing the vacuum wrapper 10a. In certain embodiments, another portion of the adhesive film 16 may be in contact with the pad region 14b, thereby sealing the vacuum wrapper 10a.

An alternating current (AC) power 150 may be provided outside the vacuum container 110 and may be used to supply an AC power between the ground layer 12 and the conductive layer 14. The AC power may be electrically connected to the pad region 14b through a power electrode connecting portion 118a. In the vacuum container 110, the power electrode connecting portion 118a may be provided to penetrate the adhesive film 16 and may be in electrical contact with the pad region 14b.

A compression part 118b may be provided near or around the power electrode connecting portion 118a and may be used to press the adhesive film 16. In certain cases, a pressure of the vacuum wrapper 10a may be higher than that of the vacuum container 110, and in this case, the vacuum wrapper 10a may be expanded. Even in this case, the sealing and the electric contacting may be stably achieved by the compression part 118b.

The vacuum wrapper 10a may include the upper film 15 and the lower film 11a. The lower film 11a may include the ground layer 12, the dielectric layer 13, and the conductive layer 14 with a hole array pattern, which are sequentially stacked. The upper film 15 and the dielectric layer 13 may be a polyethylene film. The ground layer 12 may be formed of aluminum and may be used as an outer film of the vacuum wrapper 10a, and the conductive layer 14 may be formed of aluminum and may be used as an inner film of the vacuum wrapper 10a. The vacuum wrapper 10a may include the connection member 17 formed by the thermocompression method. In the vacuum container 110, the connection member 17 may be used as a pathway for supplying the sterilant into the vacuum wrapper 10a through the coupling member 116 coupled thereto and for evacuating the sterilant from the vacuum wrapper 10a. In the vacuum container 110, the connection member 17 may be coupled to the coupling member 116. After the process of evacuating the sterilant, the thermocompressed portion 102 may be formed near the connection member 17 in the vacuum container 110 by the thermocompression method.

The conductive layer 14 may include a discharge region 14a, in which a hole array pattern is provided, and a pad region 14b extending from the discharge region 14a. The upper film 15 may include an opening which is formed to face the pad region 14b. The adhesive film 16 may be provided to be aligned to the opening. The adhesive film 16 may include a portion, which is in contact with a portion of the upper film 15 adjacent to the opening and provides a sealed space, and another portion, which is in contact with the pad region 14b and provides a sealed space.

The vacuum wrapper 10a may include the connection member 17, which is formed in the vacuum wrapper 10a by the thermocompression method. In the vacuum container 110, the connection member 17 may be used as a pathway for supplying the sterilant into the vacuum wrapper 10a through the coupling member 116 and evacuating the sterilant from the vacuum wrapper 10a. The connection member 17 may be coupled to the coupling member 116 in the vacuum container 110, and after the process of evacuating the sterilant, the thermocompressed portion 102 may be formed near the connection member 17 in the vacuum container 110 by the thermocompression method.

The connection member 17 may be used to vacuumize an internal space of the vacuum wrapper 10a or to supply a sterilant into the vacuum wrapper 10a. The connection member 17 may be inserted into an opening, which is formed through a surface of the vacuum wrapper 10a, and may be fastened to the vacuum wrapper 10a by the thermocompression method. In the vacuum container 110, the connection member 17 may be coupled to the coupling member 116 and may be used as a pathway for evacuating and supplying the sterilant from and to the vacuum wrapper 10a. After the sterilization process, a thermocompression method may be performed at a vacuum state to seal the lower and upper films 11 and 15 near the connection member 17. Accordingly, the vacuum wrapper 10a may be vacuum-packed.

A plasma purification part 144 may be provided at an output terminal of the second valve 128. The plasma purification part 144 may be configured to decompose and purify the sterilant evacuated through the second valve 128. The plasma purification part 144 may utilize the dielectric barrier discharge, inductively-coupled plasma, or capacitively-coupled plasma. An auxiliary AC power 146 may be provided to supply an AC or RF power to the plasma purification part 144. Gas decomposed by the plasma purification part 144 may be evacuated to the outside through the vacuum pump 140.

A control unit 160 may be used to control the first to fourth valves 126, 128, 132, and 134 and to control the AC power 150 and the auxiliary AC power 146. The control unit 160 may control an internal pressure of the vacuum container 110 and a pressure of the vacuum wrapper 10a, based on information regarding the pressures obtained from a pressure gauge.

Hereinafter, a sterilization process using the sterilization apparatus will be described.

A sterilization method may include loading a sealed vacuum wrapper 10a provided with a target object in the vacuum container 110 (in SS1), evacuating the vacuum container 110 and the vacuum wrapper 10a (in SS2), injecting a sterilant into the vacuum wrapper 10a, which is disposed in the vacuum container 110 and is maintained at a vacuum state (in SS5), and venting the vacuum container 110 to allow it to have the atmospheric pressure (in SS10). The vacuum wrapper 10a may be formed of a material preventing an external gas from permeating therein.

As an example, the target object may be a medical apparatus. The target object may be disposed in the vacuum wrapper 10a, and then, a border region 19 of the vacuum wrapper 10a may be sealed by a thermocompression method. The sealed vacuum wrapper 10a may be loaded in the vacuum container 110, and the vacuum container 110 may be sealed (in SS1). In this case, since there is no difference in pressure between inner and outer spaces of the vacuum wrapper 10a, the vacuum wrapper 10a may have a constant volume. The vacuum wrapper 10a may be heated up to the temperature of 50° C.-65° C. by a heater provided in the vacuum container 110.

Thereafter, the vacuum container 110 and the vacuum wrapper 10a may be evacuated (in SS2). The vacuum container 110 may be evacuated to have a base pressure, and the vacuum wrapper 10a may be evacuated to have a pressure lower than the atmospheric pressure. The fourth valve 134 may be closed, and the first to third valves 126, 128, and 132 may be opened. The vacuum wrapper 10a may include the connection member 17, which is used to inject the sterilant into the vacuum wrapper 10a or to evacuate an internal gas from the vacuum wrapper 10a. The vacuum container 110 and the vacuum wrapper 10a may be evacuated at the same time. The pressure of the vacuum container 110 may be substantially equal to or slightly lower than that of the vacuum wrapper 10a. In this case, since there is substantially no difference in pressure between inner and outer spaces of the vacuum wrapper 10a, the vacuum wrapper 10a may have a constant volume. In the case where the pressures of the vacuum container 110 and the vacuum wrapper 10a reach a desired value, the first to third valves 126, 128, and 132 may be closed.

Next, a liquid sterilant may be supplied into the vaporizer 122 (in SS3). The sterilant may be hydrogen peroxide. The vaporizer 122 may be heated up to the temperature of about 70° C.-100° C. Thus, the water contained in the supplied sterilant may be evaporated in advance.

In certain embodiments, the pressure of the vacuum container 110 may be maintained to a level higher than that of the vacuum wrapper 10a, and this may allow heat of the heated wrapping material to be more efficiently transferred to the target object. Here, the third valve 132 connected to the vacuum container 110 may be closed and the fourth valve 134 may be opened, and thus, the pressure of the vacuum container 110 may be increased by an external air injected into the vacuum container 110. At the same time, plasma may be produced in the vacuum wrapper 10a by an AC or RF power supplied from the AC power 150. In some embodiments, the plasma may be produced through a dielectric barrier discharge and the plasma may be used to activate gas in the vacuum wrapper 10a and perform a sterilization process. Furthermore, heat generated from the plasma may be used to heat the target object.

Thereafter, a vaporizer condensation process may be performed (in SS4). A liquid hydrogen peroxide supplied from the outside may have a concentration of 50 weight percent or less. The vaporizer condensation process may be performed to increase the concentration of the hydrogen peroxide. For example, the second valve 128 may be opened to evacuate the water steam evaporated in the vaporizer 122 to the outside through the vacuum pump 140. As a result of the condensation process, the concentration of the hydrogen peroxide may be increased to 70 weight percent or higher. The higher the concentration of the hydrogen peroxide, the less a process time for the sterilization. In some embodiments, the sterilant may be hydrogen peroxide whose concentration is 50 weight percent or higher.

Next, the condensed sterilant may be injected into the vacuum wrapper 10a (in SS5). For example, if the second valve 128 is closed and the first valve 126 is opened, the sterilant evaporated in the vaporizer 122 may be injected into the vacuum wrapper 10a (in SS5). If the sterilant is injected into the vacuum wrapper 10a, the vacuum wrapper 10a may have a pressure that is higher than the base pressure of the vacuum container 110. For example, the pressure of the vacuum wrapper 10a may range from several Torr to several tens Torr. In this case, owing to the difference in pressure between the inner and outer spaces of the vacuum wrapper 10a, the vacuum wrapper 10a may be expanded to have a sufficient volume for the diffusion of sterilant. The vaporized sterilant may be used to sterilize the target object. When the injection of the sterilant is finished, the pressure of the vacuum wrapper 10a may be about several tens Torr. If a predetermined amount of the sterilant is injected into the vacuum wrapper 10a, the first valve 126 may be closed.

Thereafter, the air may be injected into the vacuum container 110 such that the vacuum container 110 has a pressure higher than that of the vacuum wrapper 10a (in SS6). As the pressure of the vacuum container 110 is increased to be higher than that of the vacuum wrapper 10a, this pressure difference may lead to the shrinkage of the vacuum wrapper 10a, and the pressure of the vacuum wrapper 10a may be changed. Accordingly, owing to an increased pressure, a diffusion length of the sterilant in the target object may be increased to improve efficiency of the sterilization process. The fourth valve 134 may be opened to inject the air into the vacuum container 110.

Next, the air injected into the vacuum container 110 may be evacuated (in SS7). The evacuating of the air injected into the vacuum container 110 may be performed by opening the third valve 132.

Thereafter, plasma may be produced when the sterilant in the vacuum wrapper 10a is evacuated (in SS8). The plasma may be produced by a dielectric barrier discharge and may be used to decompose the sterilant to non-hazardous gas. Accordingly, the sterilant removing process and the purification process may be performed at the same time. In the case where the sterilant is evacuated from the vacuum wrapper 10a, the pressure of the vacuum wrapper 10a may become equal to the base pressure of the vacuum container 110. To this end, the first valve 126 and the second valve 128 may be opened. The sterilant in the vacuum wrapper 10a may be evacuated to the outside through the vacuum pump 140. In this case, the pressure of the vacuum wrapper 10a may be decreased to a level similar to the base pressure of the vacuum container 110. Accordingly, there may be substantially no difference in pressure between the inner and outer spaces of the vacuum wrapper 10a, and thus, the vacuum wrapper 10a may be shrunken. If the step of evacuating the sterilant from the vacuum wrapper 10a is finished, the first valve 126 and the second valve 128 may be closed.

Next, in the vacuum container 110, a portion 102 of the vacuum wrapper 10a adjacent to the connection member 17 may be sealed in the vacuum container 110 by a thermocompression method (in SS9). In some embodiments, the thermocompression method may be performed to seal the vacuum wrapper 10a, in which the target object is disposed. The vacuum wrapper 10a may be hermetically sealed, when the sterilant and the air are evacuated from the vacuum wrapper 10a.

Thereafter, an external air may be injected into the vacuum container 110 until the pressure of the vacuum container 110 reaches the atmospheric pressure (in SS10). For example, the first to third valves 126, 128, and 132 may be closed and the fourth valve 134 may be opened. Accordingly, the external air may flow into the vacuum container 110. As the pressure of the vacuum container 110 approaches the atmospheric pressure, the vacuum wrapper 10a may be compressed by the pressure difference.

In certain embodiments, when the external air is injected into the vacuum container 110, the external air may also be injected into the vacuum wrapper 10a. In this case, there may be substantially no difference in pressure between the inner and outer spaces of the vacuum wrapper 10a, and thus, the vacuum wrapper 10a may be maintained to a constant volume under the atmospheric pressure. In the case where the vacuum wrapper 10a has a low internal pressure and is thus shrunken under the atmospheric pressure environment, the pressure difference may lead to damage of the target object disposed in the vacuum wrapper 10a. To avoid this problem, when the venting step is performed on the vacuum container 110, the vacuum container 110 may be vented to allow it to have the atmospheric pressure.

Next, the vacuum wrapper 10a may be unloaded from the vacuum container 110 (SS11).

In the sterilization method according to some embodiments of the inventive concept, in order to secure a space for the sterilant diffusion in the vacuum wrapper 10a, the vacuum wrapper 10a may be evacuated in the vacuum container 110, a sterilant may be supplied into the vacuum wrapper 10a, and the sterilant may be evacuated from the vacuum wrapper 10a. Furthermore, if the sterilant is supplied into the vacuum wrapper 10a, the vacuum wrapper 10a may have a pressure that is higher than that of the vacuum container 110. In this case, owing to a small sterilization space, it is possible to improve efficiency of the sterilization process and reduce an amount of the sterilant used. In addition, since the outer film of the vacuum wrapper 10a is not contaminated by the sterilant, the user's safety can be improved. The vacuum wrapper 10a may be used for long time storage, compared with the conventional permeable wrapper.

Hereinafter, a sterilization process according to other embodiments of the inventive concept will be described.

According to some embodiments of the inventive concept, a sterilization method may include loading the sealed vacuum wrapper 10a with a target object in the vacuum container 110 (in SS1), evacuating the vacuum container 110 and the vacuum wrapper 10a (in SS2), producing plasma in the vacuum wrapper 10a, which is disposed in the vacuum container 110 and is maintained at a vacuum state (in SS9), and venting the vacuum container 110 to allow it to have the atmospheric pressure (in SS10). The sterilization method may further include injecting a sterilant into the vacuum wrapper 10a, which is disposed in the vacuum container 110 and is maintained at a vacuum state (in SS5).

The producing of the plasma in the vacuum wrapper 10a, which is disposed in the vacuum container 110 and is maintained at a vacuum state, may be performed under the condition in which a sterilant (e.g., oxygen or ozone) is supplied or not. Oxygen and nitrogen remaining in the vacuum wrapper 10a may be activated by the plasma and may be used to sterilize the target object. The producing of the plasma may be performed, without the supply of the sterilant, by a dielectric barrier discharge or may be performed after the supply of the sterilant.

According to some embodiments of the inventive concept, an impermeable film is used to directly inject a sterilant into a sealable wrapping pouch and thereby to improve efficiency of a sterilization process. Furthermore, the use of the impermeable film may make it possible to overcome an issue of user safety, which may occur when the sterilant is absorbed in a pouch film or remains on a surface of the pouch.

According to some embodiments of the inventive concept, an impermeable film is used to vacuumize and seal a wrapping pouch, after a sterilization process. This may make it possible to maintain a sterile state of the wrapping pouch for a longer time, compared with a wrapping pouch using a conventional semipermeability film.

According to some embodiments of the inventive concept, it is possible to produce plasma in a pouch. The plasma may be used to effectively heat a target article and purify a sterilant remaining in the pouch after a sterilization process. Accordingly, it is possible to realize an efficient and safe sterilization process.

According to some embodiments of the inventive concept, a plasma discharge in a vacuum container and a pouch is used to maximize process efficiency of a sterilization process including heating and purification steps. This may make it possible to provide a sterilizer for a fast and safe sterilization.

According to some embodiments of the inventive concept, a vacuum container is used to secure a volume of a vacuum pouch, unlike a conventional sterilization chamber. Accordingly, it is possible to reduce a volume of a small space required to perform a sterilization process on a vacuum pouch and consequently to reduce an amount of a sterilant to be used for the sterilization process.

While example embodiments of the inventive concept have been particularly shown and described, it will be understood by one of ordinary skill in the art that variations in form and detail may be made therein without departing from the spirit and scope of the attached claims.

The invention claimed is:

1. A sterilization apparatus comprising:
a vacuum wrapper containing a target object, capable of maintaining vacuum state using an impermeable film, and comprising a connection member that provides a pathway for directly supplying and evacuating a sterilant;
a vacuum container in which the vacuum wrapper is loaded;
a sterilant providing part configured to inject the sterilant into the vacuum wrapper;
a thermocompression device configured to thermocompress a portion of the vacuum wrapper adjacent to the connection member, after the evacuating of the sterilant is finished;
a heater heating the vacuum wrapper for heating the target object;
an alternating power current (AC) power source; and
a controller configured to maintain a pressure of the vacuum container to a level higher than a pressure of the vacuum wrapper such that heat of the heater is more efficiently transferred to the target object,
wherein the supplying of the sterilant and the evacuating of the sterilant are performed through a same pathway formed in the connection member,
wherein the vacuum wrapper includes an upper film and a lower film, and the lower film includes a ground layer, a dielectric layer, and a conductive layer, which are sequentially stacked, and
wherein the controller is further configured to control the AC power source to supply AC power between the ground layer and the conductive layer.

2. The sterilization apparatus of claim 1, further comprising:
a vacuum pump configured to evacuate internal air of the vacuum container and internal air of the vacuum wrapper,
wherein the sterilant injected into the vacuum wrapper is evacuated as the internal air of the vacuum wrapper is evacuated.

3. The sterilization apparatus of claim 2, wherein the sterilization apparatus is controlled such that an internal pressure of the vacuum container is lower than that of the vacuum wrapper to provide a space in which the sterilant is diffused in the vacuum wrapper.

4. The sterilization apparatus of claim 1, wherein an evacuated air to evacuate the sterilant from the vacuum wrapper is selectively purified.

5. The sterilization apparatus of claim 2, wherein selective purification is performed by purifying the air evacuated from the vacuum wrapper without purifying the air evacuated from the vacuum container.

6. The sterilization apparatus of claim 2, wherein the sterilant in the evacuated air is decomposed using a plasma discharge.

7. The sterilization apparatus of claim 2, comprising:
wherein the vacuum wrapper is shrunken by a difference in pressure between the vacuum wrapper and the vacuum container to effectively increase temperature of the target object.

8. The sterilization apparatus of claim 2, wherein, after the sterilant is injected into the vacuum wrapper, the vacuum wrapper is shrunken by a pressure difference with the vacuum container, so that concentration of the sterilant is increased.

9. The sterilization apparatus of claim 2, further comprising:
an air injection part injecting air into the vacuum container to increase an internal pressure of the vacuum container,
wherein the air injection part comprises an air filter filtering the air provided from the outside.

10. The sterilization apparatus of claim 9, further comprising:
the vacuum wrapper receives air through the air injection part.

11. The sterilization apparatus of claim 9, wherein the air filter is a high efficiency particulate air (HEPA) filter capable of removing particles and germs from the air provided from the outside.

12. The sterilization apparatus of claim 2, comprising:
a vaporizer configured to heat and vaporize the sterilant,
wherein a terminal of the vaporizer is connected to the connection member, and the terminal of the vaporizer is connected to the vacuum pump through a first valve.

13. The sterilization apparatus of claim 12, wherein the connection terminal of the vaporizer is connected to an external air injection part, and
there is a second valve between the terminal and the external air injection part.

* * * * *